US010719582B2

(12) United States Patent
Stepaniuk (10) Patent No.: US 10,719,582 B2
(45) Date of Patent: Jul. 21, 2020

(54) MEDICAL LEGAL WORKFLOW MANAGEMENT SYSTEM AND PROCESS

(71) Applicant: Stephen A. Stepaniuk, Incline Village, NV (US)

(72) Inventor: Stephen A. Stepaniuk, Incline Village, NV (US)

( * ) Notice: Subject to any disclaimer, the term of this patent is extended or adjusted under 35 U.S.C. 154(b) by 382 days.

(21) Appl. No.: 15/481,329

(22) Filed: Apr. 6, 2017

(65) Prior Publication Data

US 2017/0357759 A1 Dec. 14, 2017

Related U.S. Application Data

(60) Provisional application No. 62/349,243, filed on Jun. 13, 2016.

(51) Int. Cl.
| G06F 19/00 | (2018.01) |
| G16H 10/60 | (2018.01) |
| G06Q 30/04 | (2012.01) |
| G06Q 50/18 | (2012.01) |
| G06Q 10/10 | (2012.01) |

(52) U.S. Cl.
CPC ........... *G06F 19/328* (2013.01); *G06Q 30/04* (2013.01); *G06Q 50/18* (2013.01); *G16H 10/60* (2018.01); *G06Q 10/109* (2013.01)

(58) Field of Classification Search
CPC ...... G06F 19/328; G16H 10/60; G06Q 30/04; G06Q 50/18; G06Q 10/109
USPC ......................................................... 705/2-3
See application file for complete search history.

(56) References Cited

U.S. PATENT DOCUMENTS

| 7,296,221 B1* | 11/2007 | Treibach-Heck ........................... G06K 9/00469 715/224 |
| 2003/0097277 A1* | 5/2003 | Miller .............. G06Q 10/06311 705/2 |
| 2007/0174810 A1 | 7/2007 | Hockenberry |
| 2007/0179818 A1* | 8/2007 | Magnus ................. G06Q 10/10 705/4 |
| 2008/0154672 A1* | 6/2008 | Skedsvold ............. G06Q 10/00 705/7.15 |
| 2008/0181501 A1* | 7/2008 | Faraboschi ......... G06F 3/03545 382/179 |
| 2008/0228524 A1* | 9/2008 | Brown ................... G06Q 50/22 705/3 |
| 2009/0037224 A1* | 2/2009 | Raduchel ............... G06Q 50/24 705/3 |
| 2011/0099116 A1* | 4/2011 | Gabel .................... G06Q 10/00 705/311 |

(Continued)

OTHER PUBLICATIONS

Dallas Medical Center, "Patient Information," Aug 2014, https://www.dallasmedcenter.com/Patients-Visitors/Patient-Information.aspx (Year: 2014).*

(Continued)

*Primary Examiner* — Jason S Tiedeman
*Assistant Examiner* — Rachel F Durnin
(74) *Attorney, Agent, or Firm* — Plager Schack LLP; Mark H. Plager; Stephen Hallberg (57) ABSTRACT

A medical legal workflow management system and a medical legal workflow management process are disclosed. The medical legal workflow management system and process transfers scheduling, appointment notices, exam notes, billing invoices, and financial reports to all State and Federal forms based on a single data entry input.

10 Claims, 6 Drawing Sheets

(56) References Cited

U.S. PATENT DOCUMENTS

| | | | |
|---|---|---|---|
| 2011/0276348 A1* | 11/2011 | Ahn | G16H 10/60 |
| | | | 705/3 |
| 2014/0100878 A1 | 4/2014 | Adams | |
| 2015/0066556 A1* | 3/2015 | Dominick | G06Q 10/063114 |
| | | | 705/7.15 |
| 2016/0034647 A1* | 2/2016 | Burchianti | G06Q 10/06 |
| | | | 705/3 |
| 2016/0063197 A1* | 3/2016 | Kumetz | G06F 19/328 |
| | | | 705/3 |

OTHER PUBLICATIONS

Business Dictionary, "Letter of Collection," Jun 2008, http://www.businessdictionary.com/definition/letter-of-collection.html (Year: 2008).*

* cited by examiner

MEDICAL LEGAL WORKFLOW MANAGEMENT SYSTEM AND PROCESS

CLAIM OF BENEFIT TO PRIOR APPLICATION

This application claims benefit to U.S. Provisional Patent Application 62/349,243, entitled "Medical Legal Workflow Management System And Process," filed Jun. 13, 2016. The U.S. Provisional Patent Application 62/349,243 is incorporated herein by reference.

BACKGROUND

Embodiments of the invention described in this specification relate generally to legal compliance and workflow management in medical legal practices, and more particularly, to a medical legal workflow management system and medical legal workflow management processes.

Medical legal practices routinely have information and data (both digital and non-digital) to gather, sort, manage, maintain, and/or act on. Typically, the volume of information and data is enormous and covers a wide variety of the work carried out by a medical practice. For instance, information and data are regularly associated with medical practices such as scheduling appointments, producing medical exam reports, preparing invoices for billing, balancing financial book accounts, and maintaining volumes of paper records. As a result, managing the work associated with the information and data is labor intensive.

Existing options for medical workflow management involve a combination of hand-written notes and software. However, the existing options often result in data and information errors. For example, mistakes or errors may be made when reading hand-written notes for transcription. Such mistakes or errors in reading hand-written notes may be perpetuated when digitally transcribing the information that is read (inaccurately) from the hand-written notes. Similarly, mistakes or errors may be introduced during transcription of information that is accurately read from the hand-written notes.

Therefore, in view of the limited abilities of the existing options for medical legal workflow management, what is needed is a way to minimize mistakes and errors in the handling of information and data associated with the work practices of a medical legal practice.

BRIEF DESCRIPTION

A medical legal workflow management system and medical legal workflow management processes are disclosed. In some embodiments, the medical legal workflow management system includes a medical legal practice server computing device, a set of medical legal practice client computing devices, a medical legal practice legal form database that stores a set of State and Federal forms, and a medical legal practice workflow information database that stores several sets of medical legal practice data and information. In some embodiments, the medical legal workflow management system requires only one data entry input that transfers medical practice data and information to all State and Federal forms. In some embodiments, the medical practice data and information comprise one or more of scheduling data and information, appointment notices, exam notes, billing invoices, and financial reports.

In some embodiments, the medical legal workflow management system includes a data communication network that communicably connects the set of medical legal practice client computing devices to the medical legal practice server computing device. In some embodiments, the data communication network comprises a local data communication network that communicably connects the set of medical legal practice client computing devices to the medical legal practice server computing device within a single medical legal practice facility organized by a local area network architecture.

In some embodiments, the data communication network comprises a distributed data communication network that communicably connects the set of medical legal practice client computing devices to the medical legal practice server computing device over multiple medical legal practice facilities organized by a distributed wide area network architecture. In some embodiments, the distributed data communication network medical legal practice server computing device is associated with a first medical legal practice facility at a first physical geolocation and at least one medical legal practice client computing device is associated with a second medical legal practice facility at a second physical geolocation that is different from the first physical geolocation.

In some embodiments, the data communication network comprises a cloud data communication network that includes a cloud service network architecture.

In some embodiments, the medical legal workflow management processes include a high level medical legal workflow management process and a detailed medical legal workflow management process. In some embodiments, the high level medical legal workflow management process includes receiving a single data entry input to transfer medical practice data and information and, after the single data entry input is received, transferring the medical practice data and information to all State and Federal forms. In some embodiments, the medical practice data and information comprise one or more of scheduling data and information, appointment notices, exam notes, billing invoices, and financial reports.

In some embodiments, the detailed medical legal workflow management process includes (i) receiving demographic information for patient, attorney, and insurance provider ("all parties"), (ii) automatically transferring the demographic information into official State and Federal appointment notification forms, (iii) sending appointment notifications to all parties and a doctor of the patient, (iv) automatically notifying a staff member to call the patient to obtain a history statement, (v) requesting medical records of the patient from at least the insurance provider (and possibly the patient), (vi) sending an electronic examination form to the doctor, (vii) receiving the electronic exam form completed by the doctor, (viii) verifying the completion of the doctor-submitted electronic exam form, (ix) generating an electronic report that combines the history statement, the medical records, and the verified electronic exam form, (x) sending a notification to the doctor requesting review and approval of the electronic report, (xi) determining whether the doctor has reviewed and approved the electronic report, (xii) sending a notification to billing department to enter billing information when the doctor has affirmatively reviewed and approved the electronic report, (xiii) generating an invoice with the billing information and medical information, (xiv) sending the invoice to the insurance provider and/or the patient, (xv) determining whether the invoice is unpaid and the payment amount is past due, (xvi) generating a collection letter when the invoice is unpaid and past due, (xvii) sending the collection letter to the insurance provider and/or the patient, and (xviii) saving all of the data and information in a SQL database.

The preceding Summary is intended to serve as a brief introduction to some embodiments of the invention. It is not meant to be an introduction or overview of all inventive subject matter disclosed in this specification. The Detailed Description that follows and the Drawings that are referred to in the Detailed Description will further describe the embodiments described in the Summary as well as other embodiments. Accordingly, to understand all the embodiments described by this document, a full review of the Summary, Detailed Description, and Drawings is needed. Moreover, the claimed subject matters are not to be limited by the illustrative details in the Summary, Detailed Description, and Drawings, but rather are to be defined by the appended claims, because the claimed subject matter can be embodied in other specific forms without departing from the spirit of the subject matter.

BRIEF DESCRIPTION OF THE DRAWINGS

Having thus described the invention in general terms, reference is now made to the accompanying drawings, which are not necessarily drawn to scale, and which show different views of different example embodiments.

DETAILED DESCRIPTION

In the following detailed description of the invention, numerous details, examples, and embodiments of the invention are described. However, it will be clear and apparent to one skilled in the art that the invention is not limited to the embodiments set forth and that the invention can be adapted for any of several applications.

A medical legal workflow management system and medical legal workflow management processes are disclosed. In some embodiments, the medical legal workflow management system includes a medical legal practice server computing device, a set of medical legal practice client computing devices, a medical legal practice legal form database that stores a set of State and Federal forms, and a medical legal practice workflow information database that stores several sets of medical practice data and information. In some embodiments, the medical legal workflow management system requires only one data entry input that transfers medical practice data and information to all State and Federal forms. In some embodiments, the medical practice data and information comprise one or more of scheduling data and information, appointment notices, exam notes, billing invoices, and financial reports.

In some embodiments, the medical legal workflow management process includes receiving a single data entry input to transfer medical practice data and information and, after the single data entry input is received, transferring the medical practice data and information to all State and Federal forms. In some embodiments, the medical practice data and information comprise one or more of scheduling data and information, appointment notices, exam notes, billing invoices, and financial reports.

In this specification, there are descriptions of processes or methods that are performed by software running on one or more computing devices (e.g., a desktop computer, a server, a laptop, a tablet computing device, a smartphone, a distributed network of computing devices, etc.) to minimize mistakes and errors in the handling of information and data associated with the routine work practices of a medical legal practice. In some cases, multiple software modules are deployed on multiple computing devices (both locally networked and inter-networked via distributed computing and/or cloud computing services), thereby allowing different medical legal practice units or working groups (or departments) to work on independent parts of medical legal oriented tasks and projects with confidence that the medical legal workflows for those tasks and projects are not disturbed, mismanaged, or otherwise taken away from the managed workflow for the task or project at hand. For example, a user responsible for patient intake data may complete one part of an overall workflow in which a treating physician provides input, an attorney or representative provides other input, and still other users responsible for billing and invoicing closes out the workflow by generation of an invoice to bill the patient for services rendered. Such different medical legal practice units or working groups may be based in a single facility, across multiple related facilities, or broadly dispersed across multiple related and unrelated facilities. A variety of network configurations are described in greater detail below. However, it should be noted that for the purposes of the embodiments described in this specification, the word "method" is used interchangeably with the word "process". Methods are described, therefore, by reference to example processes that conceptually illustrate process steps for minimizing mistakes and errors in the handling of information and data associated with the work practices of a medical legal practice.

As stated above, medical legal practices are labor intensive when scheduling appointments, producing medical exam reports, billing, and maintain volumes of paper records. Embodiments of the medical legal workflow management system and processes described in this specification provide technical solutions to such problems by way of medical legal workflow management software that implements the medical legal workflow management processes to automate scheduling, exam reporting, billing, financial reporting, and Electronic Medical Record storage. In some embodiments, the process-implementing software runs on computing devices of a medical legal workflow management system.

The medical practice data and information targeted by the medical legal workflow management system and process of the present disclosure may be comprised of the following data and information elements. This list of possible constituent data and information elements is intended to be exemplary only and it is not intended that this list be used to limit the medical practice data and information targeted by the medical legal workflow management system and process of the present application to just these data and information elements. Persons having ordinary skill in the art relevant to the present disclosure may understand there to be equivalent data and information elements that may be substituted within the present disclosure without changing the essential function or operation of the medical legal workflow management system or the medical legal workflow management process.

1. Scheduling
2. Appointment notification forms
3. Medical record review
4. Medical history
5. Exam forms
6. Report editing
7. Report approval
8. Billing invoice
9. Collection letters
10. Financial reporting The various data and information elements of the medical legal workflow management system and process of the present disclosure may be related in the following exemplary fashion. It is not intended to limit the scope or nature of the relationships between the various data and information elements and the following examples are presented as illustrative examples only.

Item/Step Number #1: The scheduling department utilizes software that interacts with the medical legal workflow management software to input patient, insurance provider, and attorney demographic information.

Item/Step Number #2: The demographic information is automatically transferred into official State and Federal appointment notification forms. Email notifications automatically are sent out to all parties (e.g., patient, insurance provider, and attorney).

Item/Step Number #3: Automatic notifications to request medical records are sent out to at least the insurance provider, but possibly the patient and/or employer in the event no insurance provider. The automatic notifications are sent by any of several methods, including email and other electronic messaging systems. The medical legal workflow management software identifies when the medical records are obtained and sends a notification to the doctor.

Item/Step Number #4: The appointment notification in Step #2 automatically notifies a staff member to call the patient to obtain a history statement.

Item/Step Number #5: The doctor fills out an electronic exam form and submits the form.

Item/Step Number #6: The submitted forms are combined with the medical records and history.

Item/Step Number #7: An automatic email notification is sent to the doctor to review and approve the electronic report.

Item/Step Number #8: When the doctor approves the report, a notification is sent to the billing department. The invoice is automatically generated from the information in Steps #1-7.

Item/Step Number #9: Automatic collection letters are emailed or printed and mailed for past due invoices.

Item/Step Number #10: All the data is saved in a SQL database and can be presented in reports showing all medical legal workflow status events. Also, each doctor can view their personalized financial reports that show billing and collection amounts and dates for their cases in real time.

To make the medical legal workflow management system and process of the present disclosure, one may design and code a software application that implements the medical legal workflow management process. The software application may be deployed on a computing device and run locally in a medical practice or in a medical legal practice, or may run in a cloud-based network environment (e.g., as a private, secure, HIPAA and HITECH-compliant cloud service). The software application may be coded to access a database, such as a relational database management system in which several sets of instructions of the software application are written in Standard Query Language (SQL) or via another database programming application programming interface (API) or programming language binding. In some cases, the software application coding is informed by knowledge of doctors or other medical staff who perform medical legal examination, State and Federal official forms, and workflow management.

Embodiments of the medical legal workflow management system and process described in this specification differ from and provide technical improvements over the currently existing options. In particular, some embodiments differ because the existing medical practices and medical legal practices rely on a combination of medical software and manual or hand-written chart notes and records, which result in many errors leading to medical malpractice. In contrast, a medical legal workflow management software application that implements the medical legal workflow management process described in this specification eliminates transcription errors, replaces paper records, and is available specifically to medical legal practices.

In addition, embodiments of the medical legal workflow management system and process improve upon the currently existing options by reducing or eliminating errors in relation to State and Federal forms that are typically filled out based on a transcription of a doctor's hand-written notes, which is highly subject to errors. This is accomplished by implementation of the medical legal workflow management process in a medical legal workflow management software application that requires only one data entry input to transfer scheduling, appointment notices, exam notes, billing invoices, and financial reports, and all other related medical legal practice data and information to all State and Federal forms.

Several more detailed embodiments are described below. Section I describes medical legal workflow management processes for minimizing mistakes and errors in the handling of information and data associated with the work practices of a medical legal practice. Section II describes a medical legal workflow management system. Section III describes several example network architectures of the medical legal workflow management system. Lastly, Section IV describes an electronic system that implements some embodiments of the invention.

I. Medical Legal Workflow Management Process

In some embodiments, the medical legal workflow management processes include a high level medical legal workflow management process and a detailed medical legal workflow management process. In some embodiments, the high level medical legal workflow management process includes receiving a single data entry input to transfer medical practice data and information and, after the single data entry input is received, transferring the medical practice data and information to all State and Federal forms. In some embodiments, the medical practice data and information comprise one or more of scheduling data and information, appointment notices, exam notes, billing invoices, and financial reports.

In some embodiments, the detailed medical legal workflow management process includes (i) receiving demographic information for patient, attorney, and insurance provider ("all parties"), (ii) automatically transferring the demographic information into official State and Federal appointment notification forms, (iii) sending appointment notifications to all parties and a doctor of the patient, (iv) automatically notifying a staff member to call the patient to obtain a history statement, (v) requesting medical records of the patient from at least the insurance provider (and possibly the patient), (vi) sending an electronic examination form to the doctor, (vii) receiving the electronic exam form completed by the doctor, (viii) verifying the completion of the doctor-submitted electronic exam form, (ix) generating an electronic report that combines the history statement, the medical records, and the verified electronic exam form, (x) sending a notification to the doctor requesting review and approval of the electronic report, (xi) determining whether the doctor has reviewed and approved the electronic report, (xii) sending a notification to billing department to enter billing information when the doctor has affirmatively reviewed and approved the electronic report, (xiii) generating an invoice with the billing information and medical information, (xiv) sending the invoice to the insurance provider and/or the patient, (xv) determining whether the invoice is unpaid and the payment amount is past due, (xvi) generating a collection letter when the invoice is unpaid and past due, (xvii) sending the collection letter to the insurance provider and/or the patient, and (xviii) saving all of the data and information in a SQL database.

The medical legal workflow management processes described above include broad and general steps demonstrating how the medical legal workflow management process minimizes mistakes and errors in the handling of information and data associated with work practices of a medical practice and/or a medical legal practice. In some embodiments, the detailed medical legal workflow management process includes several more detailed steps and operations to minimize mistakes and errors in the handling of information and data associated with work practices of a medical legal practice.

Figure 1:
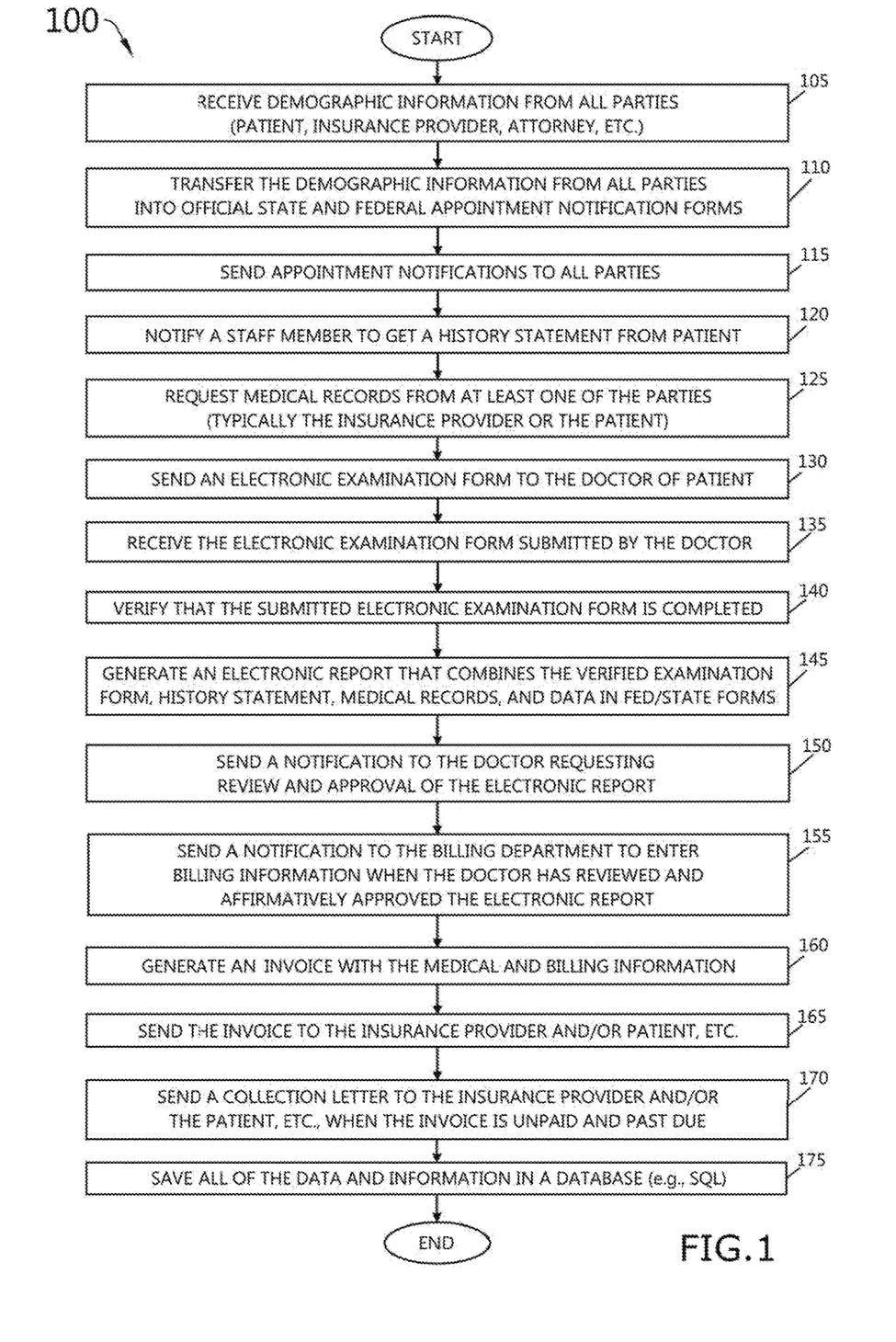
FIG. 1 conceptually illustrates a detailed medical legal workflow management process in some embodiments.

By way of example, FIG. 1 conceptually illustrates a medical legal workflow management process 100. The medical legal workflow management process of some embodiments is implemented by a medical legal workflow management software application that runs on at least one processing unit of a computing device, such as a medical legal workflow management server. In some embodiments, the medical legal workflow management process is implemented by a plurality of medical legal workflow management computer programs, applications, modules, or threads (hereinafter referred to collectively as the "medical legal workflow management software") which run on multiple processing units of a single computing device in parallel, run in a single processing unit in multi-threaded execution, or run as separate coordinated software modules on separate processing units of one or more computing devices.

In some embodiments, the medical legal workflow management process 100 starts by receiving (at 105) demographic information from all of the parties connected with a medical incident that may have legal ramifications (hereinafter referred to as the "medical legal incident"). Typically, the parties connected with the medical legal incident include a patient (the party who suffered from something that gave rise to the medical legal incident), an insurance provider (such as a workers compensation insurance provider, an employer's insurance, or a public liability insurance provider whose policy may cover general public at, e.g., a store), and an attorney (who represents the patient), but can further include an employer, a legal guardian or parent of a patient who is a legal minor, at attorney who represents the insurance provider, etc.

The demographic information may be provided, for example, by a scheduling department of a medical legal practice at the onset of initiating a new medical legal workflow case or project associated with the medical legal incident. The scheduling department may utilize software that interacts with the medical legal workflow management software. For instance, the scheduling department may run a browser that is customized with user interfaces and tools for providing demographic information to the medical legal workflow management software, which may be running on a medical legal workflow management server that is accessible to the scheduling department via a local area network ("LAN"), a wide area network ("WAN"), or a public-infrastructure network, such as the Internet ("cloud network"), configured to provide either private cloud network access or hybrid cloud network access that includes both private and public access for interacting with the medical legal workflow management system.

After the demographic information of all parties is received, the medical legal workflow management process 100 of some embodiments transfers (at 110) the demographic information into official state and federal appointment notification forms. For example, the official state and federal appointment notification forms are automatically populated with the demographic information, so as to reduce mistakes in data entry into the official forms.

In some embodiments, the official state and federal appointment notification forms are retrieved from one or more databases that are communicably connected to the medical legal workflow management server either directly or indirectly by way of a database management system. Such a database management system may include a database management software application that runs on a processing unit of the medical legal workflow management server or runs on a processing unit of a database management server computing device that is separate from, but communicatively coupled to, the medical legal workflow management server (via LAN, WAN, cloud network, etc.).

Also, the medical legal workflow management process 100 of some embodiments performs data validation processing on the demographic information prior before automatically populating the official state and federal appointment notification forms. The technical validation of the demographic information further reduces the chances for human error and thereby enhances the accuracy and validity of the overall medical legal workflow management process.

Next, the medical legal workflow management process 100 of some embodiments sends (at 115) appointment notifications to all parties. For example, the medical legal workflow management software may automatically generate and send email messages notifying all parties (e.g., the patient, the insurance provider, the attorney, a doctor of the patient, etc.) of the appointment and/or sending the official state and federal notification forms to all of the parties. In some embodiments, the medical legal workflow management process 100 also automatically notifies (at 120) a staff member to obtain a history statement from the patient. In addition, the medical legal workflow management process 100 of some embodiments automatically requests (at 125) medical records of the patient from one or more of the parties. Typically, the insurance provider is a required party to receive a notification requesting the patient's medical records, but in the absence of an insurance provider, the patient may be notified to provide medical records.

In some embodiments, the medical legal workflow management process 100 then sends (at 130) an electronic examination form to the doctor of the patient. The electronic examination form may be automatically populated with demographic information of the patient, appointment information, etc. The doctor then examines the patient and fills out the electronic examination form. Then the doctor submits the electronic examination form. At that time, the medical legal workflow management process 100 receives (at 135) the electronic examination form submitted by the doctor. Many hours, days, or weeks may pass between the moment at which the medical legal workflow management process 100 sends the electronic examination form and the moment at which the doctor submits the electronic examination form. However, to ensure timely completion of the medical legal workflow process, the medical legal workflow software may include listener agents or modules that routinely check whether the electronic examination form has been transmitted to the medical legal workflow server. The listener agents and/or modules may be embedded sub-processes of the medical legal workflow software which check status at consistent time intervals (e.g., check for incoming electronic examination forms every minute, hour, day, etc.).

In some embodiments, after the electronic examination form is received from the doctor, the medical legal workflow process 100 verifies (at 140) that the submitted electronic examination form is completed. In some embodiments, the medical legal workflow software checks all of the information entered into the electronic examination form by the doctor to ensure that all of fields requiring doctor input are completed. In some embodiments, the medical legal workflow software ensures that the form is completed by the doctor by embedding a hidden tool in the electronic examination form which is visually output to a display screen of a computing device used by the doctor only when the fields of the electronic examination form requiring doctor feedback have been completed. In some embodiments, the hidden tool is implemented by a self-executing script (computer code) that is triggered when alpha-numeric data has been input into a designated set of required fields in the electronic examination form. For example, the self-executing script may be triggered upon completion of the required fields causing a graphical user interface button or widget to become visible within the form, thereby enabling the doctor to "click" or select the button or widget to submit the completed electronic examination form which is then automatically transmitted back to the medical legal workflow server for processing by an electronic examination agent of the medical legal workflow software.

In some embodiments, the medical legal workflow management process 100 then generates (at 145) an electronic report that combines the verified electronic examination form, the patient medical history statement, the medical records, and the demographic information used in connection with the official state and federal forms. The electronic report, once generated, needs to be approved by the doctor before dissemination to others. Therefore, the medical legal workflow management process 100 of some embodiments sends (at 150) a notification to the doctor requesting review and approval of the electronic report.

When the doctor has reviewed and affirmatively approved the electronic report, the medical legal workflow management process 100 of some embodiments sends (at 155) a notification to the billing department to enter billing information in connection with at least the medical legal workflow case associated with the medical legal incident and/or billing information in connection with the doctor appointment. Next, the medical legal workflow management process 100 of some embodiments generates (at 160) an invoice with the medical and billing information. The medical legal workflow management process 100 then sends (at 165) the invoice to the insurance provider and/or the patient (and other parties as determined on a case-by-case manner). In some embodiments, the medical legal workflow management process 100 sends (at 170) a collection letter to the insurance provider and/or the patient, etc., when the invoice remains unpaid and is past due. For example, after 30 days, the unpaid invoice may become past due, which automatically triggers the medical legal workflow software to send the collection letter to the insurance provider and/or the patient (and to other parties accordingly).

In some embodiments, the medical legal workflow management process 100 saves (at 175) all of the data and information in a database. For example, a SQL database may be used to store all information for each medical legal workflow case. In some embodiments, all the information from the prior steps is saved in a database. In some embodiments, the information is continually updated in the database as new information is added. For example, the information may be saved after the invoice is generated, and then updated when a collection letter is sent. The medical legal workflow management process 100 then ends.

II. Medical Legal Workflow Management System

In some embodiments, the medical legal workflow management system includes a medical legal practice server computing device, a set of medical legal practice client computing devices, a medical legal practice legal form database that stores a set of State and Federal forms, and a medical legal practice workflow information database that stores several sets of medical practice data and information. In some embodiments, the medical legal workflow management system requires only one data entry input that transfers medical practice data and information to all State and Federal forms. In some embodiments, the medical practice data and information comprise one or more of scheduling data and information, appointment notices, exam notes, billing invoices, and financial reports.

In some embodiments, the medical legal workflow management system includes a data communication network that communicably connects the set of medical legal practice client computing devices to the medical legal practice server computing device. In some embodiments, the data communication network comprises a local data communication network that communicably connects the set of medical legal practice client computing devices to the medical legal practice server computing device within a single medical legal practice facility organized by a local area network architecture.

Figure 2:
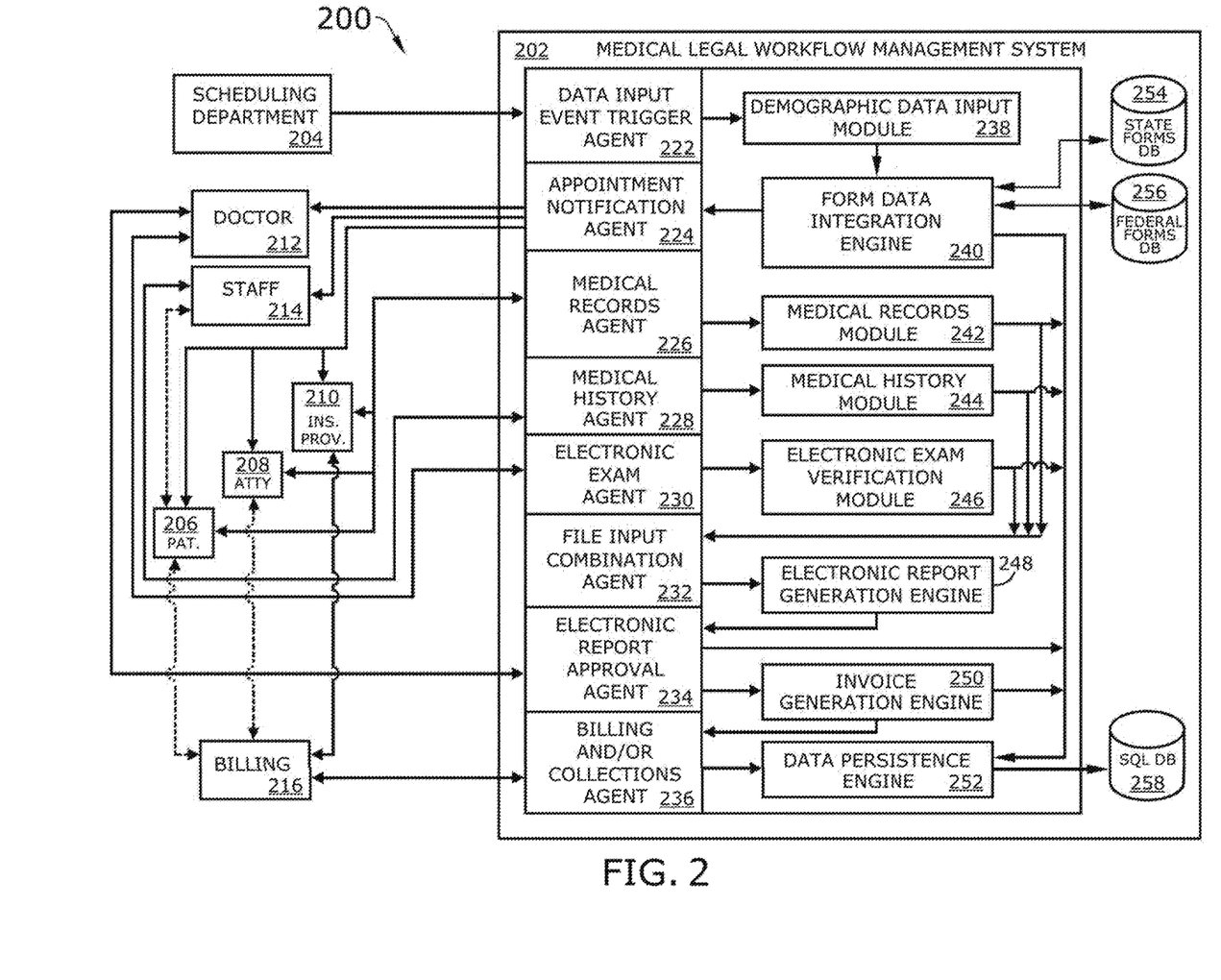
FIG. 2 includes a block diagram that conceptually illustrates a medical legal workflow management system in some embodiments.

By way of example, FIG. 2 includes a medical legal workflow management block diagram 200. The medical legal workflow management block diagram 200 conceptually illustrates a medical legal workflow management system that is utilized to minimize mistakes and errors in the handling of information and data associated with work practices of a medical legal practice.

As shown in this figure, the medical legal workflow management block diagram 200 includes a medical legal workflow management system 202 with which a scheduling department 204, a patient 206, an attorney 208, an insurance provider 210, a doctor 212, staff 214, and a billing department 216 interact. Specifically, each of the scheduling department 204, the patient 206, the attorney 208, the insurance provider 210, the doctor 212, the staff 214, and the billing department 216 use one or more computing devices to connect to and/or interact with the medical legal workflow management system 202 to perform medical legal workflow operations for any of several medical legal workflow cases or projects that are undertaken by the medical legal practice.

The computing devices used by the scheduling department 204, the patient 206, the attorney 208, the insurance provider 210, the doctor 212, the staff 214, and the billing department 216 may have interactive software installed to connect with and perform operations in relation to the medical legal workflow management system 202. Examples of the interactive software include, without limitation, browser software, medical legal workflow interfacing software, or custom medical legal workflow interfacing software tailored for specific technical workflow operations of the scheduling department 204, the patient 206, the attorney 208, the insurance provider 210, the doctor 212, or the staff 214 in connection with the medical legal workflow management system 202. For instance, the scheduling department 204 may run a browser that is customized with user interfaces and tools for providing demographic information to the medical legal workflow management system 202, the doctor 212 may run a custom medical legal workflow interfacing software application with interfaces and tools for completing an electronic examination and for reviewing and approving an electronic report, the billing department 216 may run billing and invoice communication and payment processing software that is customized to automatically communicate with parties when an invoice generation engine 250 of the medical legal workflow management system 202 triggers an invoice notification event, and the attorney 208 may use a different custom medical legal workflow interfacing software application that is customized with tools and interfaces for visually outputting a timeline or a task status list of the medical legal workflow.

The medical legal workflow management system 202 includes several databases, agents, modules, and medical legal workflow engines associated with one or more operations performed in connection with the scheduling department 204, the patient 206, the attorney 208, the insurance provider 210, the doctor 212, the staff 214, and the billing department 216. Specifically, the medical legal workflow management system 202 includes a data input event trigger agent 222, an appointment notification agent 224, a medical records agent 226, a medical history agent 228, an electronic exam agent 230, a file input combination agent 232, an electronic report approval agent 234, and a billing and collections agent 236. Additionally, the medical legal workflow management system 202 includes a demographic data input module 238, a form data integration engine 240, a medical records module 242, a medical history module 244, an electronic exam verification module 246, an electronic report generation engine 248, the invoice generation engine 250, a data persistence engine 252, a state forms database 254, a federal forms database 256, and a SQL database 258.

In some embodiments, the agents, modules, and medical legal workflow engines are components of a single medical legal workflow management server, with the databases being communicatively connected to the medical legal workflow management server. For example, a medical legal workflow management software application may be installed on the medical legal workflow management server and, when launched and running on a processing unit of the medical legal workflow management server, may carry out the operations of the medical legal workflow in relation to a medical legal workflow case.

In some other embodiments, the agents, modules, and medical legal workflow engines are individual components of a plurality of medical legal workflow management computer programs, applications, modules, or threads (hereinafter referred to collectively as the "medical legal workflow management software") which run on multiple processing units of a single computing device in parallel, run in a single processing unit in multi-threaded execution, or run as partially or entirely separate coordinated software modules on separate processing units of one or more computing devices.

For example, some or all of the agents may run on an event-based sub-system on a separate computing device that communicates with the medical legal workflow management server to coordinate workflow tasks, operations, etc., in furtherance of managing the medical legal workflow case at hand. Specifically, individual agents may listen for the specific events (or notifications of events) defined by the medical legal workflow management system 202 and, upon the occurrence of such events, may communicate with the medical legal workflow management server to trigger one or more subsequent operations in the medical legal workflow for a particular medical legal workflow case.

Similarly, the databases may run in conjunction with a database management system that is communicatively connected to the medical legal workflow management server. The databases themselves may be separate data storage devices that are organized according to the data stored on the particular storage device. For instance, the state forms database 254, the federal forms database 256, and the SQL database 258 may be separate physical data storage devices with database software having data persistence structures (e.g., relational database tables and schemas, object-oriented data schemas, etc.) defined according to the data being stored in each storage device. Alternatively, the databases may be logically different at a software level, but the data in each database may be stored (persisted) in a single physical data storage device with database software having definitions of persistence models for each data storage need (e.g., state and federal form data may be stored in separate tables of the same database, while the SQL database 258 may have a complex and detailed database persistence structure to store all the data generated, retrieved, received, or otherwise obtained for each medical legal workflow management case).

The functions of the databases, agents, modules, and medical legal workflow engines associated with operations performed in connection with the scheduling department 204, the patient 206, the attorney 208, the insurance provider 210, the doctor 212, and the staff 214 will now be described by reference to FIG. 3, which conceptually illustrates a process 300 for using the medical legal workflow management system 202. The process 300 begins when a new medical legal workflow management case (or project) is created. Each new medical legal workflow management case is typically associated with a single patient, even when multiple persons are injured from a single incident. Therefore, in this example and other examples described in this specification, each patient is associated with a separate medical legal workflow case.

In some embodiments, a first step of the process 300 involves the scheduling department utilizing the medical legal workflow interfacing software to input demographic information of all the parties associated with the medical legal workflow case. The parties typically include the patient, an attorney of the patient, and an insurance provider. A doctor later is associated with the patient, and would be part of the parties, but not until the demographic information is obtained at the start of the process 300.

As can be seen by reference to the medical legal workflow management block diagram of FIG. 2, the scheduling department 204 inputs the demographic information of all parties. When the demographic information is submitted, the data input event trigger agent 222 captures the event so that the demographic data input module 238 is informed to receive the demographic information.

Turning back to FIG. 3, the second step of the process 300 occurs after the demographic information is obtained. Specifically, the second step of the process 300 includes automatically transferring the demographic information into official State and Federal appointment notification forms. In some embodiments, the process 300 at the second step also includes automatically emailing notifications to all of the parties.

The step 2 functions are carried out by the form data integration engine 240 shown in FIG. 2. The official State and Federal notification forms are retrieved by the form data integration engine 240 from the state forms database 254 and the federal forms database 256. Then the demographic information integrated into the official State and Federal forms by the form data integration engine 240. Completion of the official State and Federal appointment notification forms with the demographic information triggers an event that is then captured by the appointment notification agent 224. In some embodiments, the appointment notification agent 224 sends the notifications to all of the parties. As shown in FIG. 2, the parties to receive the automatic notification include the patient 206, the attorney 208, the insurance provider 210, the doctor 212, and staff 214. However, in some scenarios, the notifications are sent to limited parties, such as the patient, the attorney, the doctor, and perhaps an employer (e.g., the employer may be a party when there is no insurance provider).

Completion of the official State and Federal appointment notification forms with the demographic information also results in the form data integration engine 240 transmitting the completed official State and Federal forms to the data persistence engine 252 for subsequent storing in the SQL database 258.

Figure 3:
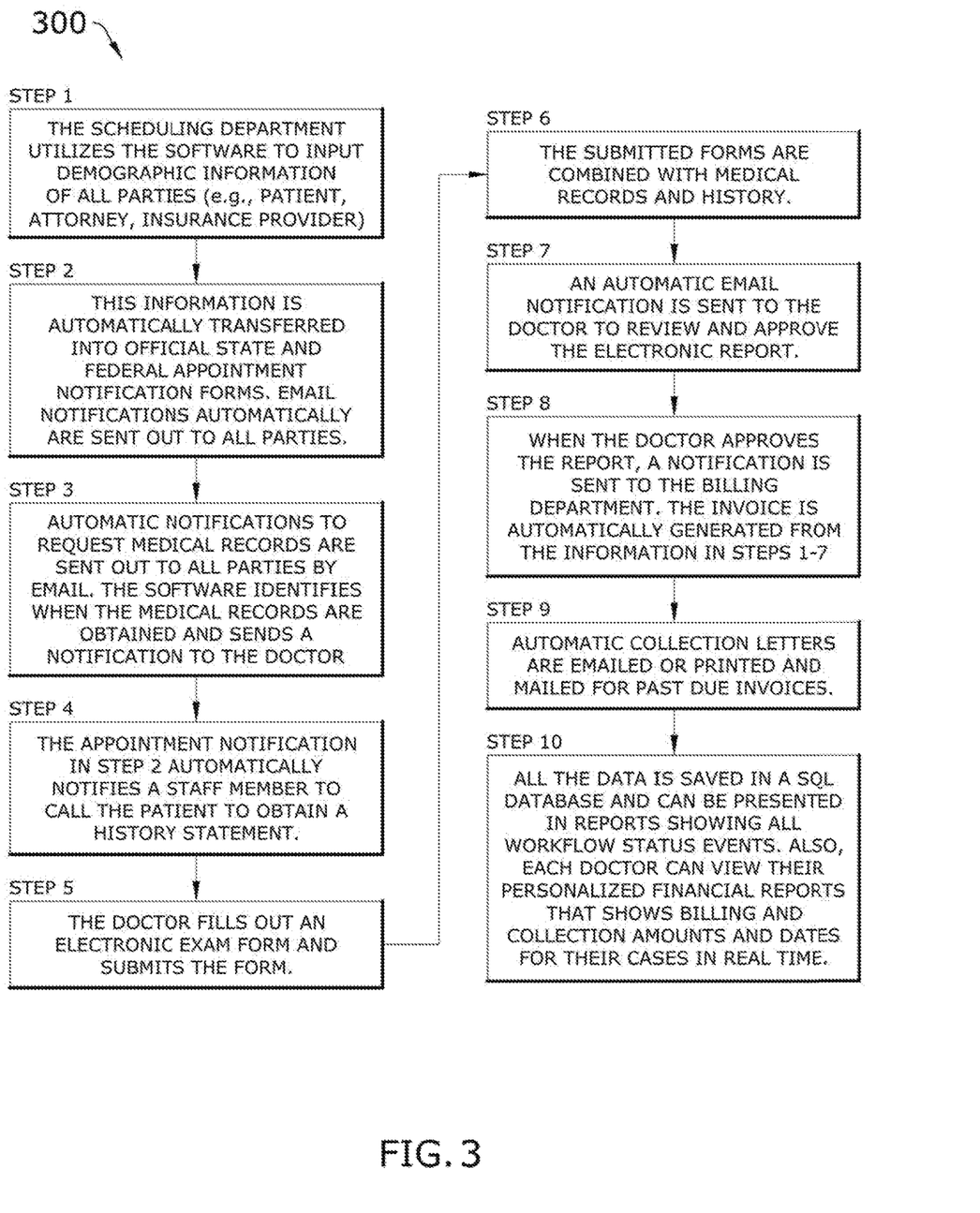
FIG. 3 conceptually illustrates a process for using the medical legal workflow management system in some embodiments.

Now as seen in FIG. 3, the third step of the process 300 includes automatically sending notifications to the parties to request medical records. The notifications may be sent via email. In some embodiments, the process 300 at the third step also includes identifying when the medical records are obtained. Then, after the medical records are obtained, the process 300 at the third step sends a notification to the doctor.

Referring back to FIG. 2, the medical legal workflow management system 202 includes a medical records agent 226 which automatically informs each of the patient 206, the attorney 208, and the insurance provider 210 of the request for medical records. In some scenarios, the medical records agent 226 only informs the insurance provider 210 and/or the patient 206 of the request for medical records. In some other cases, such as when there is no insurance provider, the medical records agent 226 informs the employer and/or the patient 206 of the request for medical records.

In some embodiments, the medical records agent 226 waits for the medical records to be received from one of the patient 206, the attorney 208, and the insurance provider 210. When the medical records agent 226 receives the medical records, an event is triggered which informs the medical records module 242 of the medical legal workflow management system 202 to retrieve or receive the medical records from the medical records agent 226. In some embodiments, the medical records module 242 then transmits the medical records to the file input combination agent 232 in preparation for generating an electronic report.

Reception of the medical records also results in the medical records module 242 transmitting the medical records to the data persistence engine 252 for subsequent storing in the SQL database 258.

Turning back to FIG. 3, the fourth step of the process 300 includes automatically notifying a staff member to call the patient to obtain a history statement. In some embodiments, the notification sent to the staff member is automatically sent when the appointment notification is sent at the second step of the process 300.

The fourth step of the process 300 is demonstrated by reference to FIG. 2. Specifically, the medical history agent 228 automatically notifies staff 214 to contact the patient 206 to obtain a history statement. Then the staff 214 calls the patient 206 for the history statement, as shown by the dashed arrow from the staff 214 to the patient 206. After the history statement is obtained, the staff 214 provides a digital textual transcription of the history statement to the medical history agent 228 of the medical legal workflow management system 202. When the medical history agent 228 receives the history statement, an event is triggered which prompts the medical history module 244 to retrieve or receive the digital textual transcription of the history statement from the medical history agent 228. In some embodiments, the medical history module 244 then transmits the digital textual transcription of the history statement to the file input combination agent 232 in preparation for generating the electronic report in combination with the medical records (which were already transmitted to the file input combination agent).

Reception of the digital textual transcription of the history statement also results in the medical history module 244 transmitting the digital textual transcription of the history statement to the data persistence engine 252 for subsequent storing in the SQL database 258.

As shown in FIG. 3, the fifth step of the process 300 includes the doctor filling out an electronic examination form and, upon completion, submitting the electronic examination form. In some embodiments, the doctor submits the completed electronic examination form by emailing the form back. In some embodiments, the doctor uses a tool to "submit" the completed form. As noted above by reference to FIG. 1, in some electronic examination forms, an embedded tool is visually output for the doctor to see and select only when all of the required fields in the electronic examination form are entered with suitable information. In some embodiments, this ensures a level of completeness and compliance which typically would involve repeated back-and-forth to finalize the electronic examination form.

The fifth step of the process 300 is demonstrated by reference to FIG. 2. Specifically, the electronic exam agent 230 sends the electronic examination form to the doctor 212 and includes instructions for the doctor 212 to submit the electronic examination form after all of the information is entered as required. Thus, after the doctor 212 submits the completed electronic examination form, the electronic exam agent 230 receives the form and triggers an event that prompts the electronic exam verification module 246 to retrieve or receive the completed electronic examination form. The electronic exam verification module 246 then automatically processes the electronic examination form to determine whether the form is completed with suitable information for each of the required fields of information. When the electronic examination form is determined by the electronic exam verification module 246 to be completed with all required and appropriate information, then the electronic exam verification module 246 transmits the completed electronic examination form to the file input combination agent 232 in preparation for generating the electronic report in combination with the medical records and the digital textual transcription of the history statement.

On the other hand, when the electronic exam verification module 246 determines that one or more fields in the electronic examination form do not include valid information, then the electronic exam agent 230 notifies the doctor 212 of the deficiencies and requests the doctor to complete the electronic examination form again. In some cases, the electronic exam agent 230 sends a fresh electronic examination form back to the doctor 212 (with no prior information included). In some other cases, the electronic exam agent 230 sends the partially completed electronic examination form back to the doctor 212 to complete the required fields that lacked information or which included inappropriate information (e.g., entering a medical license number in a field requiring the doctor's name, etc.). At that point, assuming the electronic examination form is determined by the electronic exam verification module 246 to be completed with all required and appropriate information, the electronic exam verification module 246 transmits the completed electronic examination form to the file input combination agent 232 in preparation for generating the electronic report in combination with the medical records and the digital textual transcription of the history statement.

Verification by the electronic exam verification module 246 that the electronic examination form completed by the doctor 212 is complete and accurate also results in the electronic exam verification module 246 transmitting the electronic examination form to the data persistence engine 252 for subsequent storing in the SQL database 258.

Referring again to FIG. 3, the sixth step of the process 300 includes generating an electronic report by combining the electronic examination form with the medical records and the history statement. In some embodiments, the official State and Federal appointment notification forms are also combined in the electronic report. Next, the seventh step of process 300 includes sending an automatic email notification to the doctor to review and approve the electronic report.

The sixth and seventh steps of the process 300 are demonstrated in the medical legal workflow management system 202 described by reference to FIG. 2. Specifically, the file input combination agent 232 combines the electronic examination form, the medical records, and the digital textual transcription of the history statement for processing by the electronic report generation engine 248. In some embodiments, the file input combination agent 232 also combines the official State and Federal appointment notification forms with the electronic examination form, the medical records, and the digital textual transcription of the history statement. An event is triggered when all of the files and information are combined, prompting the electronic report generation engine 248 to generate an electronic report with all of the combined files and information.

Upon generation of the electronic report, the electronic report approval agent 234 retrieves or receives the electronic report and then transmits the electronic report to the doctor 212 for review and approval.

After the doctor 212 affirmatively approves the electronic report, the electronic report approval agent 234 triggers a notification for the creation of an invoice. This is shown by the process 300 of FIG. 3, at the eighth step. Specifically, the eighth step of process 300 includes automatically generating an invoice and sending a notification to the billing department to provide the invoice to the insurance provider, the patient, and/or the attorney.

The eighth step of the process 300 is demonstrated in the medical legal workflow management system 202 described by reference to FIG. 2. Specifically, the functions of the eighth step in the process 300 are carried out by the invoice generation engine 250 which tabulates billing cost information from all of the prior steps performed in the process 300, identifies line-item and/or total cost overrides or discounts which may be associated with an insurance policy covering the medical legal workflow case for this patient (confirmed by the insurance provider), applies the line-item and/or total cost overrides or discounts to the billing information, identifies any credits that may be applied to the total billing cost, deducts any such identified credits from the total billing cost, and calculates an adjusted total billing cost for the final invoice.

Generation of the final invoice by the invoice generation engine 250 results in the final invoice being stored in the SQL database 258. That is, the invoice generation engine 250 provides the final invoice to the data persistence engine 252 to save in the SQL database 258.

In some embodiments, the invoice generation engine 250 also provides the final invoice to the billing/collections agent 236. In particular, the invoice generation engine 250 of some embodiments notifies the billing/collections agent 236 that the final invoice has been generated. This event triggers the billing/collections agent 236 in some embodiments of the legal medical workflow management system 202 to automatically notify the billing department 216 of the final invoice. For example, the billing/collections agent 236 may send an email message with the final invoice attached to the billing department 216. The email message may also include automatically generated instructions for collecting the bill and contact information for the parties to notify of the final invoice.

After obtaining the final invoice from the billing/collections agent 236, the billing department 216 notifies the insurance provider 210 of the final invoice. In addition, the billing department 216 may optionally notify the patient 206 and/or the attorney 208 of the final invoice (denoted by dashed lines). The billing department may notify the insurance provider 210 or parties by standard postal mail or electronically, via email.

In some embodiments, the billing department 216 confirms that a notification was sent to the insurance provider 210 or the parties (i.e., the insurance provider 210 and the patient 206 or the attorney 208). The confirmation can be a notification email sent to the billing/collections agent 236, a selection of a tool confirming standard post mailing of the final invoice to the insurance provider 210 and/or the parties, or an event notification that is triggered automatically when the final invoice is electronically transmitted to the insurance provider 210 and/or the parties. When the confirmation is received by the billing/collections agent 236, then the billing/collections agent 236 notifies the data persistence engine 252 of the date upon which the final invoice was provided to the insurance provider 210 (and/or parties) by the billing department 216. The date is considered the billing collections start date in order to track a collections time period for payment of the bill. The billing collections start date is then saved by the data persistence engine 252 in the SQL database 258.

Turning back to FIG. 3, the ninth step of the process 300 includes automatically sending collection letters for past due invoices. For example, when an invoice is not paid after a defined payment period (e.g., 30 days from the date of notification, 90 days from the data of notification, etc.) then the process 300 includes printing of past due notices (with subsequent standard post mailing of the past due notices) or emailing of past due notices to the insurance provider, patient, and/or attorney.

Referring back to FIG. 2, the billing/collections agent 236 in some embodiments of the medical legal workflow management system 202 operates a countdown timer for the final invoice associated with each medical legal workflow case. The countdown timer may be associated with an event that is triggered upon the countdown timer reaching zero. For example, the countdown timer may start with 30 days, count each day until the bill is paid or the timer reaches zero (if the bill is not paid), and then, if the bill has not been paid, automatically send a notification to the billing department 216 of the past due status. The billings/collections agent 236 may also instruct the data persistence engine 252 to save the date upon which a past due notice was sent out. The functions carried out by the billings/collections agent 236 may repeat for every subsequent time period in which the final invoice bill remains unpaid, at least until the bill is paid or the final invoice (unpaid) is transferred to an outside collections agency.

As shown in FIG. 3, the steps of the process 300 conclude at step ten, in which all data is saved in the SQL database (or all data that has not been saved up to this point is now saved in the SQL database). The information associated with the medical legal workflow case can then be presented in a report that shows all of the workflow status events, dates associated with each status event, and outcome of the medical legal workflow case. Also, each doctor can view personalized financial reports with billing information, collection amounts, and dates of payment and/or finalization for each medical legal workflow case.

III. Network Architectures of the Medical Legal Workflow Management System

In some embodiments, the medical legal workflow management system includes a data communication network that communicably connects the set of medical legal practice client computing devices to the medical legal practice server computing device. In some embodiments, the data communication network comprises a local data communication network that communicably connects the set of medical legal practice client computing devices to the medical legal practice server computing device within a single medical legal practice facility organized by a local area network architecture. In some embodiments, the data communication network comprises a distributed data communication network that communicably connects the set of medical legal practice client computing devices to the medical legal practice server computing device over multiple medical legal practice facilities organized by a distributed wide area network architecture.

In some embodiments, the medical legal workflow management system is a cloud network-based system that provides a cloud-based medical legal workflow management service. In some embodiments, the cloud-based system organizes the medical legal workflow management system over at least one of the local data communication network and the distributed data communication network. In some embodiments, the cloud-network medical legal workflow management system includes a cloud server computing device that hosts a medical legal workflow management cloud service when the medical legal workflow management software is running on a processor of the cloud server computing device. In some embodiments, the cloud-network medical legal workflow management system includes a virtual cloud server host that is associated with a set of cloud server computing devices. In some embodiments, the virtual cloud server host provides access to the medical legal workflow management cloud service when the medical legal workflow management software is running on one or more processors of the associated set of cloud server computing devices.

A. Cloud-Based Distributed Medical Legal Workflow Management System

In some embodiments, the cloud-based distributed medical legal workflow management system includes a medical legal workflow management server computing device that is associated with a first medical legal practice facility at a first physical geolocation, a cloud server computing device that hosts the medical legal workflow management service for one or more of a patient computing device, an attorney computing device, an insurance provider computing device, and an employer computing device to connect to and interact with over the Internet. In some embodiments, the cloud-based distributed medical legal workflow management system further includes at least one scheduling department computing device, at least one billing department computing device, at least one staff computing device, and a doctor computing device. In some embodiments, the scheduling department computing device, the billing department computing device, the staff computing device, and the doctor computing device connect to the medical legal workflow management server over a private cloud network that is enables secure network communication between distributed computing devices. In some embodiments, the scheduling department computing device is associated with a second medical legal practice facility at a second physical geolocation, the billing department computing device is associated with a third medical legal practice facility at a third physical geolocation, the staff computing device is associated with a fourth medical legal practice facility at a fourth physical geolocation, and the doctor computing device is associated with a fifth medical legal practice facility at a fifth physical geolocation. In some embodiments, the second, third, fourth, and fifth medical legal practice facilities are a single medical legal practice facility that is different from the first medical legal practice facility and the second, third, fourth, and fifth physical geolocations are different geolocations within the single medical legal practice facility.

Turning to another example of a medical legal workflow management system, FIG. 3 conceptually illustrates a multi-facility distributed network architecture of a medical legal workflow management system 300.

Figure 4:
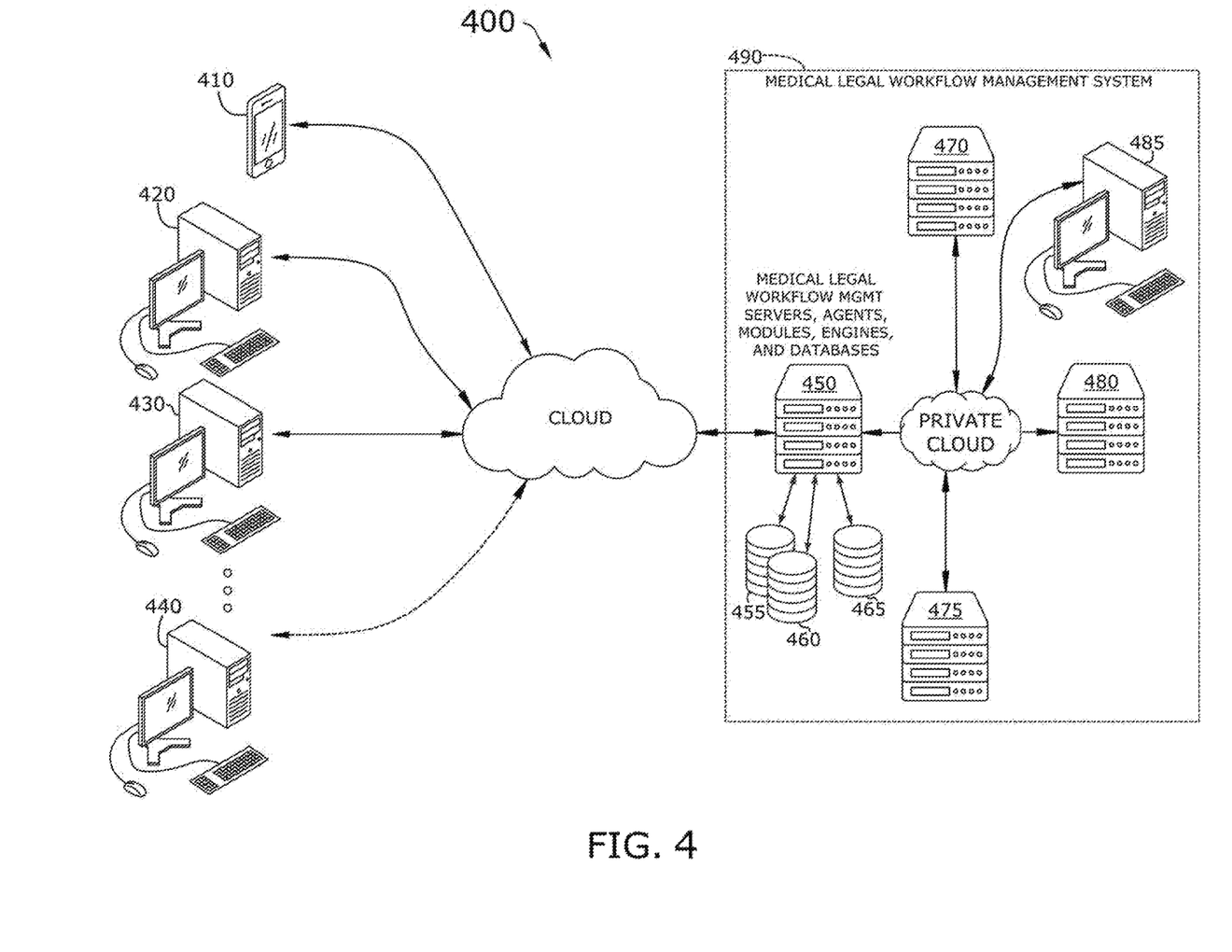
FIG. 4 conceptually illustrates a cloud-network architecture of a distributed medical legal workflow management system in some embodiments.

The next example of a medical legal workflow management system is described by reference to FIG. 4, which conceptually illustrates a cloud-network architecture 400 of a distributed medical legal workflow management system that provides medical legal workflow management to minimize mistakes and errors in the handling of information and data associated with the work practices of a medical legal practice. As shown in this figure, a set of client computing devices 410-440 access a medical legal workflow management service over a cloud network. The medical legal workflow management service is hosted on a server of the medical legal workflow management system, which in this example is a distributed medical legal workflow management system (as designated by the dashed rectangle).

The client computing devices include a patient mobile computing device 410, an attorney computing device 420, an insurance provider computing device 430, and an employer computing device 440. Each of the client computing devices 410-440 interact with the medical legal workflow management service which is hosted on at least one medical legal workflow management server 450. The medical legal workflow management server 450 is communicatively connected to a state forms database 455, a federal forms database 460, and a SQL database 465. Other computing devices used in the medical legal workflow management system connect to the medical legal workflow management server 450 over a secure private cloud network, including at least one billing department computing device 470, at least one scheduling department computing device 475, at least one staff computing device 480, and a doctor computing device 485. The medical legal workflow management system 490 is a distributed system (as designated by the dashed rectangle).

B. Cloud-Based Localized Medical Legal Workflow Management System

The cloud-based distributed medical legal workflow management system 400 demonstrates a network organization of a cloud-based medical legal workflow management system that is spread over multiple facilities at multiple, different geolocations. Another cloud-based network architecture of the medical legal workflow management system includes a localized network organization in which the medical legal workflow management system is organized over a local network within a defined limited geophysical space, with client computing devices still able to access the medical legal workflow management system over the cloud as a cloud service.

Figure 5:
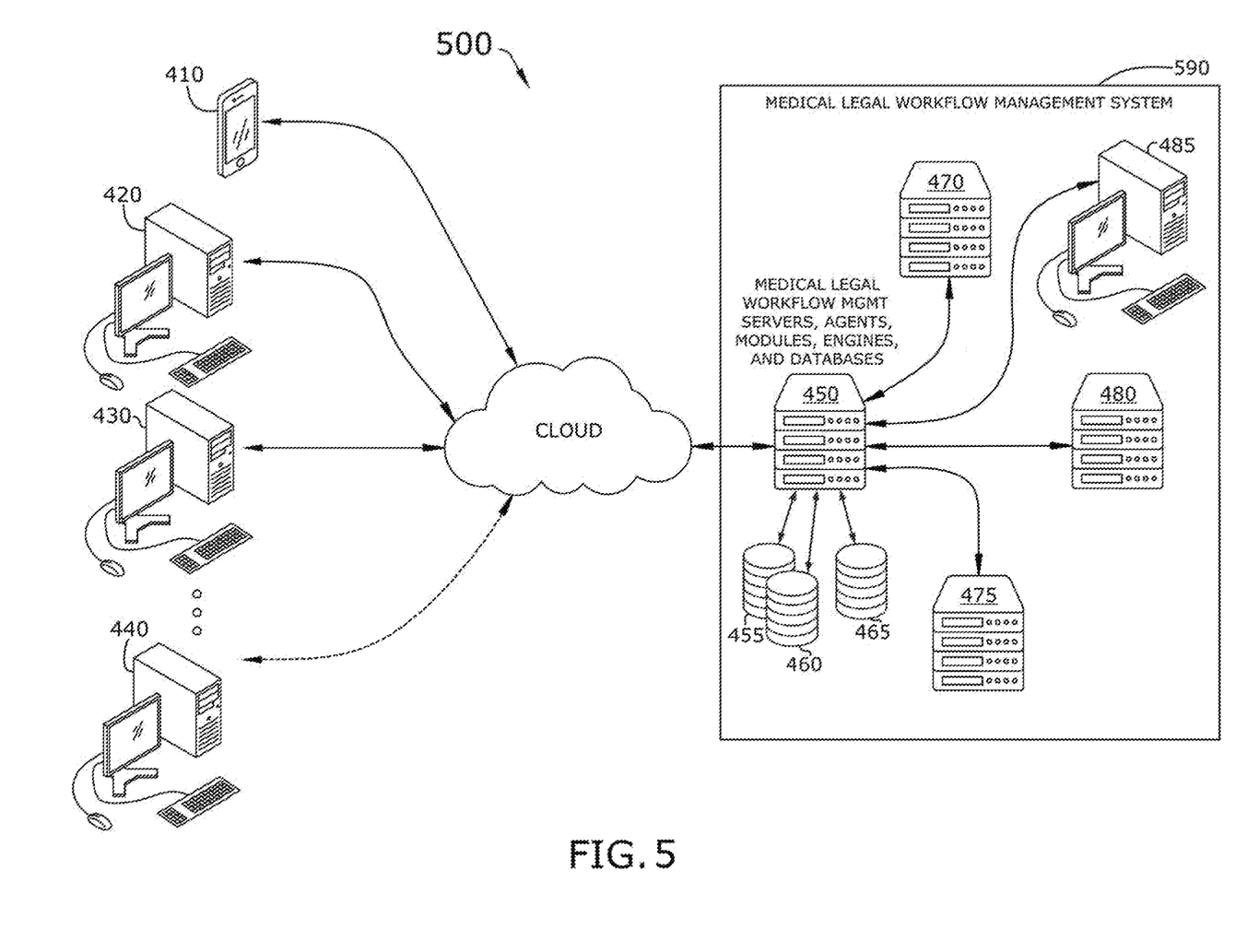
FIG. 5 conceptually illustrates a local network architecture of a localized medical legal workflow management system in some embodiments.

Such a cloud-based localized medical legal workflow management system is shown in FIG. 5, which conceptually illustrates a local network architecture 500 of a localized medical legal workflow management system 590. As shown in this figure, there is no private cloud network organization to provide network communication between different facilities at different geolocations, as shown in the distributed medical legal workflow management system 490 described by reference to FIG. 4. Instead, the network architecture is a local network architecture, such as a local area network (LAN) in a single facility, or a wide area network (WAN) over a few adjacent facilities on a single geolocation area (e.g., a campus).

III. Electronic System

Many of the above-described features and applications are implemented as software processes that are specified as a set of instructions recorded on a computer readable storage medium (also referred to as computer readable medium or machine readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the term "software" is meant to include firmware residing in read-only memory or applications stored in magnetic storage, which can be read into memory for processing by a processor. Also, in some embodiments, multiple software inventions can be implemented as sub-parts of a larger program while remaining distinct software inventions. In some embodiments, multiple software inventions can also be implemented as separate programs. Finally, any combination of separate programs that together implement a software invention described here is within the scope of the invention. In some embodiments, the software programs, when installed to operate on one or more electronic systems, define one or more specific machine implementations that execute and perform the operations of the software programs.

Figure 6:
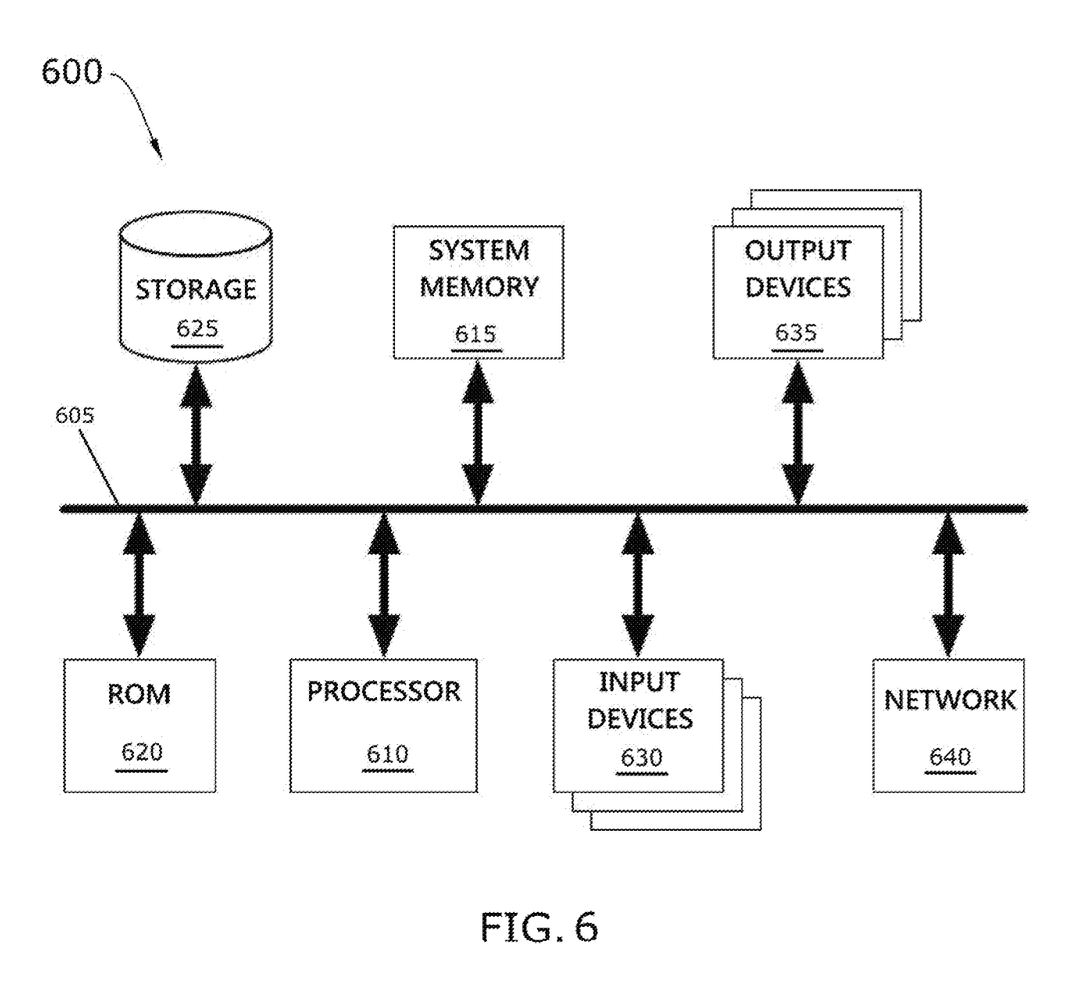
FIG. 6 conceptually illustrates an electronic system with which some embodiments of the invention are implemented.

FIG. 6 conceptually illustrates an electronic system 600 with which some embodiments of the invention are implemented. The electronic system 600 may be a computer, phone, PDA, or any other sort of electronic device. Such an electronic system includes various types of computer readable media and interfaces for various other types of computer readable media. Electronic system 600 includes a bus 605, processing unit(s) 610, a system memory 615, a read-only 620, a permanent storage device 625, input devices 630, output devices 635, and a network 640.

The bus 605 collectively represents all system, peripheral, and chipset buses that communicatively connect the numerous internal devices of the electronic system 600. For instance, the bus 605 communicatively connects the processing unit(s) 610 with the read-only 620, the system memory 615, and the permanent storage device 625.

From these various memory units, the processing unit(s) 610 retrieves instructions to execute and data to process in order to execute the processes of the invention. The processing unit(s) may be a single processor or a multi-core processor in different embodiments.

The read-only-memory (ROM) 620 stores static data and instructions that are needed by the processing unit(s) 610 and other modules of the electronic system. The permanent storage device 625, on the other hand, is a read-and-write memory device. This device is a non-volatile memory unit that stores instructions and data even when the electronic system 600 is off. Some embodiments of the invention use a mass-storage device (such as a magnetic or optical disk and its corresponding disk drive) as the permanent storage device 625.

Other embodiments use a removable storage device (such as a floppy disk or a flash drive) as the permanent storage device 625. Like the permanent storage device 625, the system memory 615 is a read-and-write memory device. However, unlike storage device 625, the system memory 615 is a volatile read-and-write memory, such as a random access memory. The system memory 615 stores some of the instructions and data that the processor needs at runtime. In some embodiments, the invention's processes are stored in the system memory 615, the permanent storage device 625, and/or the read-only 620. For example, the various memory units include instructions for processing appearance alterations of displayable characters in accordance with some embodiments. From these various memory units, the processing unit(s) 610 retrieves instructions to execute and data to process in order to execute the processes of some embodiments.

The bus 605 also connects to the input and output devices 630 and 635. The input devices enable the user to communicate information and select commands to the electronic system. The input devices 630 include alphanumeric keyboards and pointing or cursor control devices. The output devices 635 display images generated by the electronic system 600. The output devices 635 include printers and display devices, such as cathode ray tubes (CRT) or liquid crystal displays (LCD). Some embodiments include a touchscreen that functions as both an input and output device.

Finally, as shown in FIG. 6, bus 605 also couples electronic system 600 to a network 640 through a network adapter (not shown). In this manner, the computer can be a part of a network of computers (such as a local area network ("LAN"), a wide area network ("WAN"), or an Intranet), or a network of networks (such as the Internet). Any or all components of electronic system 600 may be used in conjunction with the invention.

These functions described above can be implemented in digital electronic circuitry, in computer software, firmware or hardware. The techniques can be implemented using one or more computer program products. Programmable processors and computers can be packaged or included in mobile devices. The processes and logic flows may be performed by one or more programmable processors and by sets of programmable logic circuitry. General and special purpose computing and storage devices can be interconnected through communication networks.

Some embodiments include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra-density optical discs, any other optical or magnetic media, and floppy disks. The computer-readable media may store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the invention has been described with reference to numerous specific details, one of ordinary skill in the art will recognize that the invention can be embodied in other specific forms without departing from the spirit of the invention. For instance, FIGS. 1 and 3 conceptually illustrate processes. The specific operations of each process may not be performed in the exact order shown and described. Specific operations may not be performed in one continuous series of operations, and different specific operations may be performed in different embodiments. Furthermore, each process could be implemented using several sub-processes, or as part of a larger macro process. Thus, one of ordinary skill in the art would understand that the invention is not to be limited by the foregoing illustrative details, but rather is to be defined by the appended claims.

I claim:

1. A non-transitory computer readable medium storing a medical legal workflow management program which, when executed by a processor of a computing device, manages a medical legal case in a medical legal practice, said medical legal workflow management program comprising sets of instructions for:

receiving demographic information about a patient with a medical legal case and an attorney associated with the patient;

sending the demographic information, by a data input event trigger listener agent that continuously checks for data input events and detects a particular data input event upon reception of incoming demographic information, to a demographic data input module for data validation processing to accurately populate particular forms with validated demographic information associated with the particular data input event;

providing the demographic information and references to the particular forms in a State forms database and a Federal forms database, upon validation of the demographic information by the demographic data input module, to a form data integration engine; retrieving, by way of a query issued from the form data integration engine to a database management server, the particular forms from the State forms database and the Federal forms database, wherein the particular forms retrieved from the State forms database and the Federal forms database comprise official State and Federal appointment notification forms that correspond to validated data of the demographic information;

automatically transferring, by the form data integration engine that receives the validated data upon successful data validation processing of the demographic information by the demographic data input module, the received demographic information into the official State and Federal appointment notification forms by populating the validated data from the demographic information into corresponding form fields of the official State and Federal appointment notification forms;

triggering, by the form data integration engine after populating the validated data from the demographic information into the corresponding form fields of the official State and Federal appointment notification forms, an appointment notification agent to send appointment notifications with the official State and Federal appointment notification forms accurately populated with the validated data to a plurality of medical legal workflow case parties comprising at least the patient and the attorney;

automatically requesting, by a medical records agent in connection with a medical records module, medical records of the patient from at least one medical legal workflow case party in the plurality of medical legal workflow case parties; compiling a comprehensive medical records document for the patient, by the medical records module, of all medical records of the patient received by the medical records agent from any medical legal workflow case party;

automatically sending a staff notification, by a medical history agent in connection with a medical history module, directing a medical staffer to call the patient to obtain a patient history statement; generating, by the medical history module, a medical history document for the patient, upon receiving the patient history statement after the medical staffer obtains the patient history statement by calling the patient, wherein at least a first part of the medical history document for the patient is based on the patient history statement and a second part of the medical history document for the patient is based on an accuracy check, by the medical records module, of the patient history statement in comparison to validated medical records of the patient;

notifying, by the medical records agent, a doctor for the patient when the medical records of the patient are received at the medical records module;

receiving, in realtime by an electronic exam agent, exam form data input by a doctor completing an electronic exam form in connection with the medical records of the patient;

verifying the doctor's completion of the exam form data input into the electronic exam form by a self-executing tool embedded within the electronic exam form that (i)

remains hidden while the doctor inputs the exam form data into the electronic exam form and (ii) is visually output upon completion of exam form data input by the doctor into the electronic exam form;

combining and compiling, by a file input combination agent, the comprehensive medical records document, the medical history document, and the electronic exam form into an aggregated medical case document upon receiving a verification of the exam form data input into the electronic exam form by the self-executing tool;

generating, by an electronic report generation engine, an electronic medical legal case report from the aggregated medical case document compiled by a the file input combination agent, the validated data from the demographic information from the Federal and State appointment notification forms, and the populated Federal and State appointment notification forms;

automatically generating an invoice, by an invoice generation engine that is triggered by an electronic report approval agent that sends an approval request to the doctor to approve the electronic medical legal case report generated by the electronic report generation engine, said invoice including medical and billing information for the medical legal case of the patient; and storing, by a data persistence engine, in an electronic medical legal case database that is separate from the state forms database and the federal forms database, the demographic information, the validated data, the patient history statement, the medical history document, the medical records, the electronic medical legal case report, data for a personalized financial report of the doctor in connection with the medical legal case of the patient, a billing amount for the doctor in connection with the medical legal case of the patient, a collection amount for the doctor in connection with the medical legal case of the patient, and dates of the medical legal case of the patient.

2. The non-transitory computer readable medium of claim 1, wherein the demographic information about the patient with the medical legal case and the attorney is received at the demographic data input module when the data input event trigger listener agent detects incoming demographic information from a scheduling department of the medical legal practice.

3. The non-transitory computer readable medium of claim 1, wherein the plurality of medical legal workflow case parties further comprises an insurance provider covering the patient with the medical legal case.

4. The non-transitory computer readable medium of claim 3, wherein the set of instructions for automatically requesting medical records of the patient comprises a set of instructions for requesting medical records of the patient from the insurance provider.

5. The non-transitory computer readable medium of claim 1, wherein the medical legal workflow management program further comprises a set of instructions for automatically transmitting an email notification to the doctor to review the electronic medical legal case report and determine whether to approve the electronic medical legal case report.

6. The non-transitory computer readable medium of claim 5, wherein the medical legal workflow management program further comprises a set of instructions for sending a notification to a billing department of the medical legal practice to enter billing information for the medical legal case of the patient when the doctor has reviewed and approved the electronic medical legal case report.

7. The non-transitory computer readable medium of claim 4, wherein the medical legal workflow management program further comprises a set of instructions for sending the invoice to the insurance provider covering the patient with the medical legal case.

8. The non-transitory computer readable medium of claim 7, wherein the medical legal workflow management program further comprises a set of instructions for automatically sending a collection letter to the insurance provider when the invoice is unpaid and past due.

9. The non-transitory computer readable medium of claim 1, wherein the set of instructions for receiving an electronic exam form from the doctor of the patient further comprises a set of instructions for receiving, at an electronic exam verification module by way of the electronic exam agent, a submission of the electronic exam form from the doctor of the patient, wherein the medical legal workflow management program further comprises sets of instructions for:

sending, by the electronic exam agent, the electronic exam form to the doctor of the patient before receiving the submission of the electronic exam form; and verifying, by the electronic exam verification module in connection with the self-executing tool embedded within the electronic exam form, whether the submitted electronic exam form is completed.

10. The non-transitory computer readable medium of claim 9, wherein the program further comprises sets of instructions for:

continuing with the submitted electronic exam form as the doctor-completed electronic exam form when the submitted electronic exam form is verified by the electronic exam verification module as complete; and resending, by the electronic exam agent, the electronic exam form to the doctor of the patient when the submitted electronic exam form is not complete.

* * * * *